United States Patent [19]

Krassó et al.

[11] 4,182,766

[45] Jan. 8, 1980

[54] NAPHTH[2,3-d]IMIDAZOLES

[75] Inventors: Anna Krassó, Basel; Ernst-Peter Krebs, Bottmingen, both of Switzerland

[73] Assignee: Hoffmann-La Roche Inc., Nutley, N.J.

[21] Appl. No.: 941,343

[22] Filed: Sep. 11, 1978

[30] Foreign Application Priority Data

Sep. 19, 1977 [LU] Luxembourg ............................ 78140
Jul. 28, 1978 [CH] Switzerland .......................... 8149/78

[51] Int. Cl.² .................... A61K 31/44; C07D 235/02
[52] U.S. Cl. ................................. 424/263; 546/271;
424/270; 424/273 R; 548/181
[58] Field of Search ........................ 546/271; 424/263

[56] References Cited
FOREIGN PATENT DOCUMENTS

| | | | |
|---|---|---|---|
| 2504252 | 8/1975 | Fed. Rep. of Germany | 546/271 |
| 2548340 | 7/1977 | Fed. Rep. of Germany | 546/271 |
| 1234058 | 6/1971 | United Kingdom | 546/271 |
| 1500043 | 2/1978 | United Kingdom | 546/271 |
| 1525958 | 9/1978 | United Kingdom | 546/271 |

OTHER PUBLICATIONS

Hankovszky et al., Chem. Abstracts, vol. 71, item No. 112863f (1969).

*Primary Examiner*—Alan L. Rotman
*Attorney, Agent, or Firm*—Jon S. Saxe; George M. Gould; William G. Isgro

[57] ABSTRACT

Imidazole derivatives of the formula

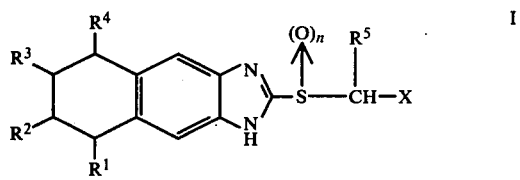

wherein $R_1$, $R_2$, $R_3$, $R_4$, $R_5$, X and n are as hereinafter set forth, and pharmaceutically acceptable acid addition salts thereof, are described. The compounds of formula I are useful in the treatment of gastric ulcers.

11 Claims, No Drawings

NAPHTH[2,3-d]IMIDAZOLES

BRIEF SUMMARY OF THE INVENTION

The invention relates to imidazole compounds useful in the treatment of gastric ulcers, and with the preparation of such compounds. The compounds of the invention are characterized by the formula

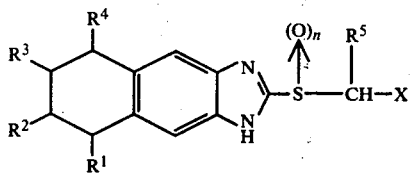

wherein $R_1$, $R_2$, $R_3$ and $R_4$ are each hydrogen or both of the pairs $R_1$ plus $R_2$ and $R_3$ plus $R_4$ are additional carbon to carbon bonds, n is 0 or 1, $R_5$ is hydrogen or lower alkyl and X is 2-pyridyl, 2-pyridyl substituted by a lower alkyl group, 2-imidazolyl, 2-imidazolinyl, 2-thiazolyl, 2-thiazolinyl, 4(5)-imidazolyl and 4(5)-imidazolyl substituted with a lower alkyl group,
and pharmaceutically acceptable acid addition salts thereof.

DETAILED DESCRIPTION OF THE INVENTION

The invention relates to imidazole derivative of the formula

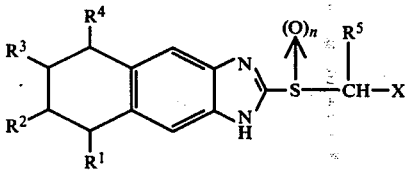

wherein $R_1$, $R_2$, $R_3$ and $R_4$ are each hydrogen or both of the pairs $R_1$ plus $R_2$ and $R_3$ plus $R_4$ are additional carbon to carbon bonds, n is 0 or 1, $R_5$ is hydrogen or lower alkyl and X is 2-pyridyl, 2-pyridyl substituted by a lower alkyl group, 2-imidazolyl, 2-imidazolinyl, 2-thiazolyl, 2-thiazolinyl, 4(5)-imidazolyl and 4(5)-imidazolyl substituted with a lower alkyl group
and pharmaceutically acceptable acid addition salts thereof.

When $R_1$, $R_2$, $R_3$ and $R_4$ are each hydrogen, the compounds of the invention are characterized by the formula

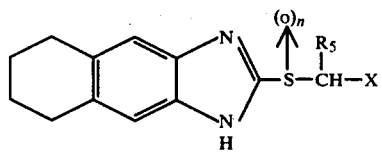

When both $R_1$ plus $R_2$ and $R_3$ plus $R_4$ are an additional carbon to carbon bond, the compounds of the invention are characterized by the formula

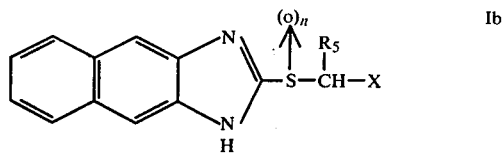

As used herein, "lower alkyl" denotes straight- or branched-chain saturated, aliphatic hydrocarbon radicals containing from 1 to 7, preferably from 1 to 4 carbon atoms, for example, methyl, ethyl, n-propyl, isopropyl and the like.

In accordance with the invention, preferred compounds are those compounds of formula I wherein X is 2-pyridyl or 2-pyridyl substituted with a lower alkyl group, preferably methyl. Further preferred compounds are those wherein the aforementioned 2-pyridyl contains a methyl substitutent and said methyl group is at the 5 or 6 position. Additional preferred compounds, in accordance with the present invention, are those compounds of formula I wherein both of the pairs $R_1$ plus $R_2$ and $R_3$ plus $R_4$ are additional carbon to carbon bonds and n is zero. Preferably, $R_5$ in formula I is hydrogen.

Specifically preferred compounds are 2-[<(5-methyl-2-pyridyl)methyl>thio]-1H-naphth(2,3-d)imidazole and 2-[(2-pyridylmethyl)thio]-1H-naphth(2,3-d)imidazole, or their respective pharmaceutically acceptable acid addition salts.

The compounds of formula I wherein n is zero are prepared by reacting a compound of the formula

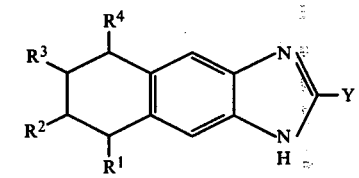

wherein $R_1$, $R_2$, $R_3$ and $R_4$ have the meanings given above and Y is as described hereinafter, with a compound of the formula

wherein $R_5$ and X have the meanings given above and one of Y and Y' is a mercapto and the other is a leaving group.

Many of the starting materials of formulas II and III are known compounds. Those compounds falling within the scope of formulas II and III which are not previously known can be conveniently prepared by methods analogous to the preparations of the known compounds given in the literature, or by methods described hereinafter.

Examples of suitable leaving groups represented by Y and Y' in the above formulas include halogens, preferably chlorine bromine or iodine, acyl radicals, for example, residues of strong organic sulfonic acids, for instance, of an arylsulfonic acid, for example, tosyloxy, or an alkylsulfonic acid, for example, mesyloxy; alkylmercapto groups, for example, methylmercapto; alkylsulfinyl groups, for example, methylsulfinyl and the like.

The reaction of a compound of formula II above with a compound of formula III is conveniently carried out in the presence of a suitable solvent that is inert under the reaction conditions utilized as described hereinafter. The reaction may further be carried out in the presence of a suitable base. Suitable bases include, for example, inorganic bases such as sodium or potassium hydroxide, sodium or potassium hydride and the like, organic bases such as tertiary amines, for example, triethylamine and the like.

Suitable solvents for the above described reaction include, for example, alcohols, preferably lower alkanols such as, methanol and ethanol; mixtures of such alcohols with water; ethers, such as, tetrahydrofuran; halogenated hydrocarbons, such as, methylene chloride and chloroform; and the like. A preferred solvent is dimethylformamide.

The reaction of the compounds of formulas II and III may be carried out at a temperature between the ambient temperature and the boiling temperature of the reaction mixture. It is preferred to carry out the reaction, however, at a temperature at or close to the boiling point of the reaction mixture.

In an advantageous embodiment of the process of the present invention, a compound of formula II wherein Y is mercapto is initially converted into the corresponding alkali metal derivative, for example, by reaction with sodium or potassium hydroxide. The reaction with a compound of formula III wherein Y' is the acid radical of a reactive ester is then carried out. In a preferred embodiment the reaction is carried out without the presence of a base by heating the reactants in the presence of dimethylformamide.

The compounds of formula I wherein n is 1 are prepared by oxidizing a compound of formula I wherein n is zero and thereby converting the sulfur atom into a sulfinyl group. Oxidizing agents conventionally recognized as being useful for such purposes are utilized. Such oxidizing agents include, for example, peracids such as m-chloroperbenzoic acid; peroxides such as hydrogen peroxide; peresters; sodium metaperiodate; selenium dioxide; manganese dioxide; and the like.

The oxidation of the compount of formula I wherein n is zero is conveniently carried out utilizing one of the above named oxidizing agents in an organic solvent which is inert under the reaction conditions. Suitable solvents include, for example, halogenated hydrocarbons such as methylene chloride, chloroform, dichloroethane and the like or a hydrocarbon such as benzene. When hydrogen peroxide is utilized as the oxidizing agent, the reaction may be carried out in aqueous medium which may be acidified with, for example, acetic acid and the like. In any event, the oxidizing agent is preferably utilized in slight excess with regard to the substrate being oxidized. The oxidation reaction is preferably carried out at ambient temperature or below.

Depending on factors such as the structure of the starting material and the chosen embodiment of the process as described herein, certain compounds of formula I, that is, those which contain an asymmetric center, can exist as optical isomers or as racemates. Further, when the compounds of formula I contain two or more asymmetric centers, they can exist as diastereoisomeric mixtures or mixtures of racemates. Such diastereoisomeric mixtures and mixtures of racemates can be separated and the racemates resolved according to procedures conventional in the art, for example, by fractional crystallization of salts with optically active acids.

The compounds of formula I may, depending on the process conditions utilized as described herein, be obtained as either the free base or in the form of acid addition salts. When it is desired to obtain the compounds of formula I in the form of their pharmaceutically acceptable acid addition salts, such salts are readily obtained by reaction of the free base with a suitable acid. Suitable acids include, for example, inorganic acids, such as, hydrochloric acid, sulfuric acid, hydrobromic acid, phosphoric acid and the like or organic acids, such as, citric acid, acetic acid, succinic acid, maleic acid, p-toluenesulfonic acid or the like. If desired, a salt of a compound of formula I can be converted into the free base or, if necessary, to a pharmaceutically acceptable salt by conventional procedures recognized in the art.

The imidazole derivatives of formula I inhibit gastric acid secretion and have been demonstrated to be effective in inhibiting the formation of stress induced ulcers. Therefore, the compounds of formula I are useful therapeutically in the treatment of gastric ulcers. For such use the compounds of formula I or their pharmaceutically acceptable acid addition salts are administered as pharmaceutically acceptable compositions in combination with pharmaceutically acceptable, therapeutically inert inorganic or organic carrier materials suitable for the enteral or parenteral administration of medicaments. Such preparations may be in solid form, for example, tablets, capsules or suppositories or may be in liquid form, that is, as solutions, suspensions or emulsions.

Suitable art-recognized therapeutically inert pharmaceutical carrier materials useful in the preparation of the compositions of the present invention include, for example, water, gelatin, lactose, starch, talc, magnesium stearate, vegetable oils, polyalkyleneglycols and the like. The pharmaceutical compositions of the present invention may be sterilized and may contain art-recognized adjuvants, for example, preservatives, stabilizers, wetting or emulsifying agents, salts to adjust osmostic pressure, buffers and the like. Such compositions may likewise contain other therapeutically useful substances. Acid addition salts of compounds of formula I wherein n is one will preferably not be combined into pharmaceutical compositions containing water because they have been found to be relatively unstable in aqueous media.

The activity of the novel imidazole derivatives of the present invention as inhibitors of the secretion of gastric acid in warm-blooded animals has been and can be demonstrated in the following manner. A part of the stomach fundus of dogs is separated from the remaining stomach in the form of a pouch according to the Heidenhain technique described by Rudick et al in J. Surgical Research, vol. 7, pp 383–398 (1967). The pouch is fitted with a steel canula conducted externally through the abdominal wall and the operation is allowed to heal. Utilizing a conscious dog prepared as above, gastric secretion is stimulated by an infusion of 4-methylhistamine dihydrochloride ($40\mu$/kg per hr., i.v.) which selectively stimulates histamine $H_2$ receptors. When volumes of fifteen minute samples of gastric secretion and pH levels appear constant, the test substance is administered orally and samples again taken. Under these conditions, when 2[<(5-methyl-2-pyridyl)methyl>thio]-1H-naphth(2,3-d)imidazole and 2-<(2-pyridyl-methyl)-thio>1H-naphth(2,3-d)imidazole were utilized as the test substance, each demonstrated as effective therapeutic dosage of approximately 3 mg./kg. In the context of this procedure, an effective therapeutic dosage may be defined as the amount of test substance administered per os which causes as inhibition of from 60-80% of the acid secretion produced by the administration of 4-methylhistamine.

The useful activity of the compounds of formula I as inhibitors of the formation of stress-induced gastric ulcers in warm-blooded animals was and can be demonstrated by administrating various dosages of individual compounds per os to female rats of approximately 140 to 160 g and thereafter placing the animals in a water bath at 22.5° C., 7 cm deep for six hours, conditions which have been shown to produce gastric ulcers in untreated animals. After six hours in the water, the animals were sacrificed and the incidence of ulcers noted. The $ED_{50}$, that is, the dosage at which 50% of the 10 rats utilized per dosage are protected against stress-induced ulcers by the test compound was then determined according to the Probit method.

In the above-described procedure when 2-[<(5-methyl-2-pyridyl)methyl>thio]-1H-naphth-(2,3-d)imidazole as utilized as the test substance, the effective dosage was 31 mg./kg. per os and for 2-<(2-pyridylmethyl)thio>-1H-naphth(2,3-d)imidazole it was 12 mg./kg. per os. Furthermore, the foregoing compounds demonstrated in the mouse an $LD_{50}$ of 8000 mg/kg. per os and >5000 mg./kg. per os, respectively.

Compositions containing the imidazole derivatives of formula I can be utilized in the therapeutic treatment of gastric ulcers in a considerable range of dosage depending on the individual clinical situation. Generally, however, it is contemplated in that a sufficient amount of such a composition be administered orally to provide from about 100 mg. to about 400 mg. of a compound of formula I daily and, when intravenous administration is contemplated, a daily dosage of from about 5 mg. to about 20 mg. of a compound of formula I.

The following examples further illustrate the invention. Unless otherwise noted, all temperatures given are in degrees Centigrade.

EXAMPLE 1

10. 1 g of 1H -naphth[2,3-d]imidazole-2-thiol are suspended in 100 ml of alcohol in a 250 ml volume sulphonating flask equipped with a stirrer, thermometer, cooler and dropping funnel. A solution of 4.0 g. of sodium hydroxide in 50 ml of water was then added dropwise, and a clear solution formed. The solution was then heated to boiling, 8.2 g of 2-chloromethyl-pyridine-hydrochloride were added, and the resulting mixture was boiled under reflux overnight. The reaction mixture was then concentrated by evaporation, the residue was taken up in 600 ml of ethyl acetate and 200 ml of water, and the ethyl acetate phase was washed twice with 200 ml of water, dried over sodium sulphate, and concentrated by evaporation in vacuo. The residue was recrystallised once from ethyl acetate/petroleum ether and provided 2-[(2-pyridylmethyl)thio]-1H-naphth[2,3-d]imidazole having a melting point of 165°-167°; the hydrochloride melts at 230°-231°.

Preparation of the Starting Substances.

125.0 g of 2,3-dihydroxynaphthalene was suspended in 3.5 l of $NH_3$ (25%) and shaken for 60 hours at 240° and under a pressure of 30 bars $N_2$. The suspension was suction filtered, washed with 1.5 of water, and then dissolved in 7 l of ethyl acetate. The ethyl acetate solution was extracted twice with in each case 1 l of 3 N NaOH and twice with in each case 1 l of $H_2O$, dried over $Na_2SO_4$, filtered through charcoal, and the decolourised filtrate was concentrated by evaporation in vacuo at 40°. The residue was stirred for 1 hour in 400 ml of acetonitrile at room temperature, suction filtered, and dried. 128 g of the 2,3-diaminonaphthalene thus obtained were suspended in 900 ml of ethanol. A solution of 51.0 g of KOH in 160 ml of water was added dropwise while stirring vigorously. After stirring for 10 minutes at room temperature, 71.6 g of carbon disulphide was added dropwise. The reaction mixture was stirred for 1 hour at approx. 20°, and then stirred further overnight at reflux temperature. After adding 91.0 g of KOH in 370 ml of water, full solution took place. The reaction mixture was filtered through 50 g of charcoal and the filtrate was diluted with 900 ml of water. 295 ml of glacial acetic acid in 295 ml of water was added dropwise at an internal temperature of 60°-70° while stirring. The suspension was next stirred for 1 hour at the same temperature, and then cooled in an ice bath and suction filtered. The residue was washed with 300 ml of water and then with 100 ml of ethanol. After drying in vacuo at 60°, 158.0 g of crude product was obtained, which was suspended in 600 ml of dioxane, stirred for 1 hour at approx. 20°, and then suction filtered. The precipitate was washed in succession with 100 ml of dioxane and 300 ml of ether. After drying in vacuo at 60°, 148.1 g of 1H-naphth[2,3-d]-imidazole-2-thiol was obtained. M.p. 303°-305°.

120 g of 2-hydroxymethylpyridine were stirred in 2 l of absolute benzene. 100 ml of thionylchloride was slowly added dropwise at 0.5° and the reaction mixture was stirred overnight at approx. 20°. The mixture was then cooled to 0°-5° and suction filtered. The precipitate was dissolved hot in 1000 ml of ethanol, filtered over charcoal, and concentrated by evaporation at 50°. The residue was dissolved in 400 ml of acetonitrile, stirred at room temperature for 1 hour, and the 2-chloromethylpyridine-HCl was suction filtered. M.p. 121°-123°.

EXAMPLE 2

9.4 g of 2-[(2-pyridylmethyl)thio]-1H-naphth[2,3-d]imidazole were suspended in 250 ml of methylenechloride in a 1 liter volume four-necked round bottomed flask equipped with a stirrer, thermometer, dropping funnel and calcium chloride tube.

A solution of 6.7 g of m-chloroperbenzoic acid in 150 ml of methylenechloride was added dropwise while stirring vigorously and cooling with ice/methanol, and the reaction mixture was then stirred for a further 5-7 hours at 0.5°. The mixture was then washed three times with 100 ml of sodium bicarbonate solution, washed with 200 ml of sodium chloride solution until neutral, dried over sodium sulphate, and concentrated by evaporation in vacuo. The residue was recrystallised from 500 ml of toluene and provided 2-[(2-pyridylmethyl)sulphinyl]-1H-naphth[2,3-d]imidazole having a m.p. of 145°-146°.

EXAMPLE 3

0.92 g of 2-chloro-1H-naphth[2,3-d]imidazole and 0.57 g of 2-mercaptomethylpyridine were heated under reflux for 18 hours in 15 ml of ethanol and 4.5 ml of 1 N caustic soda. 50 ml of water were added to the reaction solution, which was then extracted twice with a total amount of 50 ml of ethyl acetate. The organic phases were washed with saturated sodium chloride solution, dried over magnesium sulphate, and evaporated to dryness on a rotary evaporator. Crystallisation from 50 ml of acetonitrile provided 0.68 g of 2-[(2-pyridylmethyl)-thio]-1H-naphth[2,3-d]imidazole having a m.p. of 169°–170°.

Preparation of the Starting Material 16.2 g of 2-hydroxy-1H-naphth[2,3-d]imidazole were heated for 3 hours under reflux in 170 ml of phosphorusoxychloride. The reaction solution was concentrated by evaporation, decomposed with water, and adjusted with ammonia until alkaline. The suction filtered residue was chromatographed on 500 g of silica gel. 2.5 g of 2-chloro-1H-naphth[2,3-d]imidazole were eluted with ethyl acetate. Crystallisation from methanol provided a product having a m.p. >300°.

EXAMPLE 4

0.45 g of 2-methylthio-1H-naphth[2,3-d]imidazole and 0.64 g of 2-mercaptomethylpyridine were heated for 40 hours under reflux in 10 ml of ethanol. 10 ml of water were added to the homogeneous solution and the precipitate formed was filtered off. 0.50 g of 2-[(2-pyridylmethyl)thio]-1H-naphth[2,3-d]imidazole having a m.p. of 170° was obtained.

Preparation of the Starting Material.

20.0 g of 1H-naphth[2,3-d]imidazole-2-thiol and 4.0 g of sodium hydroxide were heated for 1 hour under reflux and in 150 ml of ethanol with 6.5 g of methyl iodide. The reaction solution was diluted with 500 ml of water and the precipitated product was suction filtered. Crystallisation from dioxane provided 12.0 g of 2-methylthio-1H-naphth[2,3-d]imidazole haing a m.p. of 242°–244°.

EXAMPLE 5

0.165 g of 2-(methylsulphinyl)-1H-naphth[2,3-d]imidazole and 0.090 g of 2-mercaptomethylpyridine was heated for 1 hour reflux in 5 ml of ethanol and 0.72 ml of 1N caustic soda. The reaction solution was concentrated by evaporation and chromatographed on silica gel. 0.050 g of 2[(2-pyridylmethyl)thio[-1H-naphth[2,3-d]imidazole was eluted with ethyl acetate.

Preparation of the Starting Material.

A solution of 4.2 g of m-chloroperbenzoic acid in 100 ml of methylenechloride was added dropwise at 0°–5° to 4.3 g of 2-(methylthio)-1H-naphth[2,3-d]imidazole in 500 ml of methylenechloride. The reaction solution was stirred for 90 minutes at 0°, washed twice with aqueous potassium bicarbonate solution and once with saturated sodium chloride solution, dried over magnesium sulphate, and concentrated by evaporation on a rotary evaporator. Crystallisation from acetonitrile gave 2.3 g of 2-(methylsulphinyl)-1H-naphth[2,3-d]imidazole having a m.p. of 194°.

EXAMPLE 6

90.0 g of 1H-naphth[2,3-d]imidazole-2-thiol in 200 ml of dimethylformamide were heated at 95°. 80.1 g of 2-chloromethyl-5-methylpyridine-hydrochloride were added to the homogeneous solution and the resultant solution was kept at 95° for 10 minutes. After cooling to room temperature, 1 l of ether was added and the mixuture was suction filtered. The residue was taken up in 2 N potassium bicarbonate solution and extracted with a total amount of 21 of methylenechloride. The organic phases were washed with saturated sodium chloride solution, dried over magnesium sulphate, and then concentrated by evaporation on a rotary evaporator. The residue was recrystallised from 21 of alcohol. 106 g of 2-/[(5-methyl-2-pyridyl)-methyl]thio/-1H-naphth[2,3-d]imidazole having a m.p. of 185°–186° was obtained.

Preparation of 2-chloromethyl-5-methylpyridine-hydrochloride.

11.5 g of 2,5-dimethylpyridine-N-oxide in 5 ml of acetic acid were added dropwise to 18 ml of acetic anhydride pre-heated to 120°. The reaction solution was boiled under reflux for a further 45 minutes, concentrated by evaporation on a rotary evaporator, and distilled at 8 mm Hg/115°. 14.0 g of 2-acetoxymethyl-5-methylpyridine was obtained.

14.0 g of 2-acetoxymethyl-5-methylpyridine were heated under reflux for 90 minutes in a solution of 4.5 g of sodium hydroxide in 150 ml of water. The cooled solution was saturated with sodium chloride and extracted with a total amount of 100 ml of chloroform. The organic phases were washed with saturated sodium chloride solution, dried over magnesium sulphate, and concentrated by evaporation at 40°/16 mm Hg. The oil obtained distilled at 12°/8 mm Hg. 8.7 g of 2 -hydroxymethyl-5-methylpyridine were obtained.

8.7 g of 2-hydroxymethyl-5-methyl-pyridine were added dropwise at a reaction temperature of 0°–10° to 18 ml of thionyl chloride. The reaction solution was next stirred for 15 hours at room temperature and then concentrated by evaporation on a rotary evaporator. The residue was treated with activated charcoal in alcohol and crystallised from alcohol-ether. 11.5 g of 2-chloromethyl-5-methylpyridine-hydrochloride having a m.p. 145°–146° was obtained.

EXAMPLE 7

3.2 g of sodium hydroxide and 7.2 g of 2-chloromethyl-4-methyl-pyridine-hydrochloride were added to 8.1 g of 1H-naphth[2,3-d]imidazole-2-thiol in 80 ml of ethanol and 40 ml of water, and the whole was heated under reflux for 2 hours. The reaction solution was concentrated by evaporation and distributed between water and ethyl acetate/tetrahydrofuran. The organic phases were washed with saturated sodium chloride solution, dried over magnesium sulphate, and evaporated to dryness on a rotary evaporator. The oily residue was crystallised from toluene. 6.5 g of 2-/[(4-methyl-2-pyridyl)methyl]thio/-1H-naphth[2,3-d]imidazole having a m.p. of 170°–172° were obtained.

2-/[6-Methyl-2-pyridyl)methyl]thio/-1H-naphth[2,3-d]imidazole having a m.p. of 119°–120° was prepared in a similar manner.

EXAMPLE 8

6.4 of NaOH in 40 ml of water was added to 0° to 8 g of 1H-naphth[2,3-d]imidazole-2-thiol in 80 ml of ethanol and 8.72 g of rac-2-(1-chloroethyl)-pyridine in 40 ml of ethanol was added dropwise while stirring. After boiling for 12 hours under reflux, the solution was concentrated by evaporation in vacuo and the residue was worked up with ethyl acetate-water. From 11.5 g of crude product and after purification on silica gel and crystallisation from ethyl acetate, 6.0 g of rac-2-/[1-(2-pyridyl)ethyl]thio/-1H-naphth[2,3,-d]imidazole having a m.p. of 129°–133° were obtained.

The optical resolution of the racemate was effected by means of (+) or (−)-di-0,0'-p-toluoyl-tartaric acid (DITTA) in ethyl acetate-toluene (1:1).

(−) (RR) DITTA-salt with (+) Base m.p. 142°–143°, $[\alpha]_D = +93.7°$ (in methanol, c=1.0)

(+) Base m.p. 136°–137°, $[\alpha]_D = +413.8°$ (+) (SS) DITTA-salt with (−) Base m.p. 136°–137°, $[\alpha]_D = 92.1°$, (−) Base m.p. 135.5–136.5°, $[\alpha]_D = -408.6°$

EXAMPLE 9

10.0 g of 1H-naphth[2,3-d]imidazole-2-thiol and 9.6 g of 2-chloromethyl-5-ethyl-pyridine-hydrochloride were heated for 2 hours under reflux in 200 ml of ethanol and 100 ml of 1 N caustic soda. The reaction solution was concentrated by evaporation on a rotary evaporator, taken up in 250 ml of water, and extracted 3 times with 100 ml of ethyl acetate. The organic phases were washed with saturated sodium chloride solution, dried over magnesium sulphate, and evaporated to dryness. Crystallisation from acetonitrile gave 8.2 g of 2-/[(5-ethyl-2-pyridyl)methyl]thio/-1H-naphth[2,3-d]-imidazole having a m.p. of 156°–157°.

EXAMPLE 10

2.24 g of KOH in 10 ml of water followed by 3.28 g of 2-chloromethylpyridine-HCl in 20 ml of ethanol were added to 4.09 g of 5,6,7,8-tetrahydro-1H-naphth[2,3-d]imidazole-2-thiol in 50 ml of ethanol. After boiling under reflux for 12 hours, the solution was concentrated by evaporation in vacuo and the residue was worked up in the normal manner with ethyl acetate-water. The ethyl acetate phase concentrated by evaporation to approximately 50 ml and cooled to 0° gave 4.8 g of crystal having a m.p. of 95°–97°, which was recrystallised from 50 ml of acetonitrile: 4.15 g of 5,6,7,8-tetrahydro-2-[(2-pyridylmethyl)thio]-1H-naphth[2,3-d]-imidazole, of m.p. 98°–101°.

Preparation of the Starting Material.

6.16 g of KOH dissolved in 20 ml of water, followed by 7.3 ml of carbon disulphide were added dropwise at 0° to a solution of 16.2 g of 5,6,7,8-tetrahydro-2,3-diaminonaphthalene in 100 ml of isopropanol and 20 ml of ethanol. After boiling for 2 hours under reflux, the pH was adjusted to 3–4 with glacial acetic acid, and the precipitated white crystals were suction filtered at 0°. The crystals were dissolved in 200 ml of isopropanol, and the solution was boiled under reflux for ½ hour and then suction filtered at 0°. 17.8 g of 5,6,7,8-tetrahydro-1H-naphth[2,3-d]imidazole-2-thiol, having a m.p. of 282°–289° were obtained.

EXAMPLE 11

A solution of 1.7 g of m-chloroperbenzoic acid in 50 ml of methylenechloride was added dropwise at a reaction temperature of 0°–5° to 3.2 g of 2-/[(5-ethyl-2-pyridyl) methyl]thio/-1H-naphth[2,3-d]imidazole in 200 ml of methylenechloride. The reaction solution was stirred for 3 hours at 0°, then washed twice with aqueous potassium bicarbonate solution and once with saturated sodium chloride solution, and finally evaporated to dryness. The green residue was treated with activated charcoal in acetonitrile/methanol, and crystallised from the same solvent mixture. 2.1 g of 2-/[(5-ethyl-2-pyridyl)-methyl]-sulphinyl/-1H naphth[2,3-d]imidazole having a m.p. of 177° were obtained.

EXAMPLE 12

1.1 g of 2-hydroxymethylthiazol were dissolved in 50 ml of chloroform and stirred for 2 hours at 20° with 0.82 ml of thionylchloride, and then boiled under reflux for 30 minutes. After concentration by evaporation in vacuo at 40°, the residue was taken up in 20 ml of ethanol and the solution was reevaporated. A solution of 1.91 g of 1H-naphth[2,3-d]imidazole-2-thiol in 50 ml of ethanol, 2.14 g of KOH and 10 ml of water was added to the crystals of chloromethylthiazol hydrochloride obtained, and the whole was boiled for 2 hours under reflux. The solvent was removed in vacuo and the residue was worked up with ethyl acetate-water. After recyrstallisation twice from acetonitrile, 1.3 g of 2-[(2-thiazolyl-methyl)thio]-1H-naphth[2,3-d]imidazole having an m.p. of 153°–157° was obtained.

EXAMPLE 13

1.0 g of 1H-Naphth[2,3-d]imidazole-2-thiol and 0.8 g of 2-chloromethylimidazole-hydrochloride were heated for 1½ hours at 90° in 20 ml of dimethylformamide. The precipitate formed was filtered off, washed with a small amount of acetonitrile, and dissolved in 2 N sodium bicarbonate solution. The aqueous phase was extracted three times with 30 ml of ethyl acetate. The organic phases were washed with saturated sodium chloride solution, dried over magnesium sulphate, and then concentrated by evaporation. The residue was recrystallised from 150 ml of acetonitrile. 150 mg of 2-[(Imidazole-2-ylmethyl)thio]-1H-naphth[2,3-d]imidazole having a melting point of 172° was obtained.

EXAMPLE 14

10.0 g of 1H-Naphth[2,3-d]imidazole-2-thiol and 8.0 g of 2-chloromethylimidazoline-hydrochloride were heated for 3 hours at 90° in 50 ml of dimethylformamide. The reaction mixture was cooled to room temperature and then diluted with 200 ml of toluene. The residue was suctioned filtered, washed well with toluene, and crystallised from 700 ml of methanol, with the addition of 300 ml of ether. 10.3 g of 2-[(2-Imidazoline-2-ylmethyl)thio]-1H-naphth[2,3-d]imidazol-dihydrochloride having an m.p. of 227°–228° were obtained.

EXAMPLE 15

2.38 g of thionylchloride in 10 ml of chloroform were added at 0° to 2.5 g of 2-(1-hydroxyethyl)-thiazole in 50 ml of absolute chloroform, and stirred for 1 hour at 0°, for 30 minutes at 20°, and for 1 hour under reflux. After removing the solvent in vacuo the residue was resolved in 20 ml of ethanol and the solution was re-evaporated. A mixture of 4.0 g of 1H-naphth-[2,3-d]imidazole-2-thiol, 80 ml of ethanol, 4.48 g of KOH and 40 ml of water was added to the remaining oil, and the whole was boiled under reflux for 12 hours. After evaporation in vacuo, the residue was taken up in 300 ml of water and extracted three times with 200 ml of methylenechloride. The organic phases evaporated to dryness crystallised from benzene. 1.8 g of 2-/[1-(2-thiazolyl)ethyl]thio/-1H-naphth[2,3-d]imidazole having an m.p. of 184°–186° was obtained after recrystallising twice from benzene.

EXAMPLE 16

2.85 g of 5,6,7,8-Tetrahydro-1H-naphth[2,3-d]imidazole-2-thiol were boiled under reflux for 12 hours with 50 ml of ethanol, 2.24 g of KOH, 10 ml of water and 2.5 g of 2-chloromethyl-5-methyl-pyridine, and then concentrated by evaporation in vacuo, and finally worked up with methylenechloride-water. From 4.8 g of residue and after recrystallisation from 80 ml of acetonitrile, 3.78 g of 5,6,7,8-tetrahydro-2-/[(5-methyl-2-pyridyl)methyl]-thio/-1H-naphth[2,3-d] imidazole having an m.p. of 135°–136° were obtained.

5,6,7,8-Tetrahydro-2-/[1-(2-pyridyl)-ethyl]-1H-naphth[2,3,-d]imidazole having an m.p. 124°–125°, was prepared in a similar manner.

EXAMPLE 17

A solution of 1.725 g of m-Chloroperbenzoic acid in 50 ml of methylenechloride was added at 0°-5° to 3.05 g of 2-/[(5-methyl-2-pyridyl)methyl]thio/-1H-naphth[2,3-d]imidazole and 3.0 g of potassium carbonate in 300 ml of methylenechloride. The reaction mixture was next stirred for 30 minutes at 0°, then washed with aqueous potassium bicarbonate solution and saturated sodium chloride solution, dried over magnesium sulphate, and concentrated by evaporation at 40°/16 mm Hg. The residue was recrystallised twice from acetonitrile. 1.6 g of 2-/[5-Methyl-2-pyridyl)methyl]sulphinyl/-1H-naphth[2,3,-d]-imidazole having an m.p. of 181° was obtained. 5,6,7,8-Tetrahydro-2-[(2-pyridylmethyl)-sulphinyl]-1H-naphth[2,3-d]imidazole having an m.p. of 155°–156° was prepared in a similar manner.

EXAMPLE 18

6.7 g of 4-Chloromethyl-5-methyl-imidazole-hydrochloride were added to 8.0 g of 1H-naphth[2,3,-d]imidazole-2-thiol in 20 ml of dimethylformamide at 90°. After 10 minutes, the mixture was cooled to a room temperature and ether was added. The precipitate was suction filtered and recrystallised from water-ethanol. 6.5 g of 2-/[(5-Methylimidazole-4-yl)methyl]thio/-1H-naphth[2,3-d]imidazole-dihydrochloride having a m.p. of 265°–267° was obtained.

EXAMPLE 19

35 ml of a 10% solution of m-chloroperbenzoic acid were added dropwise at 0° to 6.2 g of 5,6,7,8-tetrahydro-2-/[1-(2-pyridyl)ethyl]-thio/-1H-naphth[2,3-d]imidazole in 50 ml of methylenechloride. After stirring for 3 hours at 0°, the precipitated material was suction filtered, suspended in acetonitrile, refiltered under suction, and washed with ether and then with petroleum ether. 2.7 g of 5,6,7,8-tetrahydro-2-/[1-(2-pyridyl)ethyl]sulphinyl/-1H-naphth[2,3-d]imidazole having a m.p. of 152°–153° was obtained.

The following compounds were prepared in a similar manner:

5,6,7,8-Tetrahydro-2-/[(5-methyl-2-pyridyl)methyl]-sulphinyl/-1H-naphth[2,3-d[imidazole, m.p. 188°–189°, 2-/[1-(2-Pyridyl)ethyl]sulphinyl/-1H-naphth[2,3-d]-imidazole, m.p. 172°–173°.

EXAMPLE A

Pharmaceutical tablets were prepared from the following formulation:

| Ingredient | Mg. Per Tablet |
|---|---|
| 2-[<(5-methyl-2-pyridyl)methyl>thio]1H-naphth (2,3-d)imidazole | 50 |
| Lactose | 100 |
| Maize Starch, white | 48 |
| Magnesium Stearate | 2 |
| Total Tablet Weight | 200 |

The active ingredient, the lactose and a portion of the maize starch were thoroughly mixed and thereafter blended with a paste prepared from a second portion of the maize starch and water. The resulting mixture was granulated, dried and passed through a seive. The resulting granulate was mixed with the remainder of the maize starch and then with the magnesium stearate. The mixture was blended on a suitable apparatus until homogeneous and pressed into tablets each weighing 200 mg.

EXAMPLE B

In accordance with the procedure of example A, pharmaceutical tablets were prepared from the following formulation:

| Ingredient | Mg. Per Tablet |
|---|---|
| 2-<(2-pyridylmethyl)thio>-1H-naphth (2,3-d)imidazole | 100 |
| Lactose | 150 |
| Maize Starch, white | 145 |
| Magnesium Stearate | 5 |
| Total Tablet Weight | 400 mg. |

We claim:

1. A compound of the formula

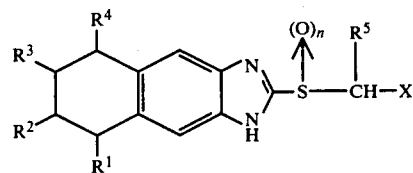

wherein $R_1$, $R_2$, $R_3$ and $R_4$ are each hydrogen or both of the pairs $R_1$ plus $R_2$ and $R_3$ plus $R_4$ are additional carbon to carbon bonds, n is 0 or 1, $R_5$ is hydrogen or lower alkyl and X is 2-pyridyl or 2-pyridyl substituted by a lower alkyl group, or a pharmaceutically acceptable acid addition salt thereof.

2. A compound in accordance with claim 1, wherein X is 2-pyridyl or 2-pyridyl substituted by a lower alkyl group.

3. A compound in accordance with claim 2, wherein the 2-pyridyl is substituted by a methyl group.

4. A compound in accordance with claim 3, wherein the methyl group is on the 5 or 6 position of said 2-pyridyl radical.

5. A compound in accordance with claims 1, 2, 3 or 4 wherein each of the pairs $R_1$ plus $R_2$ and $R_3$ plus $R_4$ is an additional carbon to carbon bond.

6. A compound in accordance with claim 1, 2-[<(5-methyl-2-pyridylmethyl>thio]-1H-naphth(2,3-d)imidazole or a pharmaceutically acceptable acid addition salt thereof.

7. A compound in accordance with claim 1, 2-<(2-pyridylmethyl) thio>-1H-naphth(2,3-d)imidazole or a pharmaceutically acceptable acid addition salt thereof.

8. A pharmaceutical composition for the treatment of gastric ulcers comprising a therapeutically inert carrier and, a therapeutically effective amount of a compound of the formula

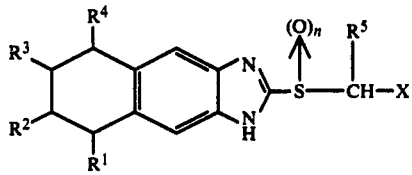

wherein $R_1$, $R_2$, $R_3$ and $R_4$ are each hydrogen or both of the pairs $R_1$ plus $R_2$ and $R_3$ plus $R_4$ are additional carbon to carbon bonds, n is 0 or 1, $R_5$ is hydrogen or lower alkyl and X is 2-pyridyl or 2-pyridyl substituted by a lower alkyl group, or a pharmaceutically acceptable acid addition salt thereof.

9. A composition in accordance with claim 8 wherein the compound of formula I is 2-[<(5-methyl-2-pyridyl)-methyl>thio]-1H-naphth (2,3-d)imidazole or a pharamaceutically acceptable acid addition salt thereof.

10. A composition in accordance with claim 8, wherein the compound of formula I is 2-<(2-pyridyl-methyl)thio>-1H-naphth(2,3-d) imidazole or a pharmaceutically acceptable acid addition salt thereof.

11. A method for the treatment of gastric ulcers which comprises administering to a host requiring such treatment as effective amount of compound of the formula

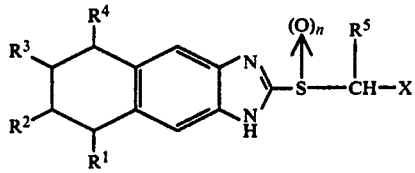

wherein $R_1$, $R_2$, $R_3$ and $R_4$ are each hydrogen or both of the pairs $R_1$ plus $R_2$ and $R_3$ plus $R_4$ are additional carbon to carbon bonds, n is 0 or 1, $R_5$ is hydrogen or lower alkyl and X is 2-pyridyl or 2-pyridyl substituted by a lower alkyl group, or a pharmaceutically acceptable acid addition salt thereof.

* * * * *